United States Patent [19]

Brooks

[11] 4,047,437
[45] Sept. 13, 1977

[54] CONTINUOUS ROW AVERAGE SAMPLING METHOD AND APPARATUS FOR STATIONARY SOURCE GAS STREAMS

[75] Inventor: Edward F. Brooks, Lawndale, Calif.

[73] Assignee: TRW Inc., Redondo Beach, Calif.

[21] Appl. No.: 716,317

[22] Filed: Aug. 20, 1976

[51] Int. Cl.² .............................................. G01N 1/26
[52] U.S. Cl. .............................................. 73/421.5 A
[58] Field of Search ................... 73/421.5 R, 421.5 A

[56] References Cited

U.S. PATENT DOCUMENTS

| 3,459,047 | 8/1968 | Sumansky | 73/421.5 A |
| 3,486,382 | 12/1969 | Vivares et al. | 73/421 R |

Primary Examiner—S. Clement Swisher
Attorney, Agent, or Firm—John J. Connors

[57] ABSTRACT

Continuous row average sampling of a stationary source gas stream is accomplished with the aid of a tubular sampling probe extending across the gas stream flow path in a transverse plane of the path and having sampling port means forming a longitudinally extending sampling port row through which gas is drawn into the probe. The sampling port means preferably comprise one or more ports spanned by a porous filter medium and are designed to produce a pressure drop which is substantially uniform along the port row and relatively large in comparison to any internal or external pressure changes which occur along the probe so as to maintain a uniform gas sampling rate along the port row.

4 Claims, 9 Drawing Figures

CONTINUOUS ROW AVERAGE SAMPLING METHOD AND APPARATUS FOR STATIONARY SOURCE GAS STREAMS

BACKGROUND OF THE INVENTION

1. Field

This invention relates generally to the art of gas sampling for analysis purposes and more particularly to a novel row average gas sampling apparatus for continuously sampling a stationary source gas stream.

2. Prior Art

Continuous monitoring of the total gaseous mass emissions and individual gas species emissions from stationary sources is becoming ever increasingly important for both process control and compliance with emission standards. Such stationary source emissions, of course, generally constitute high volume gas flows through large ducts. As a consequence, it is impossible or impractical to monitor the total gas flow, and the required emissions data must be obtained by extrapolating data obtained from a relatively small volume representative sample of the total gas flow.

For any given gas concentration distribution in a stationary source effluent gas stream, it is a simple matter to select a sampling array which will yield a representative gas sample suitable for analyses and extrapolation of the resulting emissions data to the total flow volume. Problems arise when more than one species must be sampled and the gas distributions change as a function of time.

One of the greatest difficulties with regard to continuous sampling of a stationary source gas stream, for example, is to effectively handle the temporal changes which occur in the gas concentration distribution since such changes are primarily a function of combustion characteristics and air leakage and hence extremely difficult, if not impossible, to predict. Temporal changes in velocity distribution are not such a problem, since velocity distributions are primarily a function of local flow duct geometry, which is normally fixed, and hence capable of relatively accurate prediction. Another major methodological difficult involved in continuous sampling of a stationary source effluent gas stream involves stratification of both gas velocity and composition.

Current stationary source gas stream sampling techniques for large flow ducts tend to fall into either of two extremes. At one extreme are precision manual tranverse sampling procedures and single point sampling techniques. At the other extreme are flow proportional sampling techniques.

The manual traverse sampling procedures are performed in accordance with the requirements stated in "Standards of Performance for New Stationary Sources," Environmental Protection Agency, set forth in the Federal Register, Vol. 36, No. 159, Part II. This manual sampling procedure, while precise and accurate, is timing consuming, costly, and totally unsuited to continuous monitoring of process streams and stack emissions, for example.

Single point sampling techniques are often utilized for continuous monitoring applications and are characterized by the advantages of relative simplicity and economy. The available single point sampling data for stationary source effluent streams, however, shows stratification levels in the streams on the order of 10 to 15 percent and very poor temporal repeatability. On this basis, single point sampling is undesirable due to accuracy limitations.

As noted earlier, at the opposite extreme of the existing stationary source gas sampling techniques are flow proportional sampling techniques. These sampling techniques require a relatively large multipoint sampling array with means for monitoring or sensing the local gas stream flow velocity at each sampling point. Sample analysis may be accomplished by utilizing either standard wet chemistry techniques or continuous gas analyzers. If wet chemistry techniques are used, the sampling rate at each sampling point must be proportional to the local gas stream flow velocity. If continuous gas analyzers are used, the gas concentration at each sampling point is measured by the corresponding analyzer and then multiplied by the local gas flow velocity to obtain the local mass flow rate. In either event, the flow proportional sampling techniques are complex and costly to the point of being totally impractical for many industrial process control and emission standards compliance applications.

Accordingly, there is a need for an economically feasible and technically acceptable compromise between the above sampling extremes for sampling a stationary source gas stream to derive data which may be extrapolated to determine with acceptable accuracy the total gaseous mass flow or emission and/or the total individual constituent gas flows or emissions in the gas.

SUMMARY OF THE INVENTION

This invention provides a novel stationary source gas stream sampling method and apparatus involving a sampling technique referred to herein as spatial or row average sampling in contrast to flow proportional sampling. Briefly, spatial or row average sampling involves sampling a stationary source gas stream within a flow confining duct along one or more sampling rows extending across the gas stream flow path, preverably in the direction of highest stratification. The sampling rate is kept substantially uniform along the entire sampling row, and all the sample gas extracted along the sample row or rows is combined to provide a composite sample which is conducted to a gas analyzer for measurement of the total and constituent gas concentration of the sample. The gas flow velocity is determined independently of the gas sampling and is multiplied by the gas concentration data to obtain total and constituent gas sample data which may be extrapolated to obtain the total gaseous mass flow or emissions and the total individual constituent flow or emissions in the gas streams.

This spatial sampling technique has the advantages that the gas sampling action and the gas flow velocity measurement may be totally independent of one another, and the number and location of flow sensors required for the gas flow velocity measurement is determined by the flow duct geometry, not the sampling requirements. In some cases, a single flow sensor may suffice. As a consequence, the spatial or row average sampling technique is relatively simple and economical. Moreover, as will be seen, the accuracy of this technique compares very favorably with the more complex and costly flow average techniques and is thus ideally suited to industrial sampling applications for process control and emissions standards compliance.

The spatial or row average stationary source gas stream sampling apparatus of the invention comprises a tubular sampling probe having a longitudinally extending sampling port row opening to a common longitudinal passage in the probe and an outlet for connection to a vacuum source and a gas analyzer.

The probe is installed in the gas stream flow duct with the sampling port row extending in the desired direction of the gas flow path, and preferably in the direction of highest gas stratification in the duct. In some cases a single probe may suffice for satisfactory sampling. In other cases, a plurality of probes may be desirable. The outlets of all the probes are connected to a vacuum source for evacuating the probes to induce gas inflow through the sampling port rows of the probes and then from the probes to a gas analyzer in a manner such that all of the sample gas which enters the probe or probes through the sampling port row or rows is combined and mixed and then conducted to the analyzer for measurement of the total and constituent gas concentration, as mentioned earlier.

A basic requirement of spatial or row average sampling resides in the fact that the sampling rate must remain substantially uniform along the full length of each sampling row and hence along the sampling port row of each sampling probe. According to an important feature of the invention, this uniformity of sampling rate along the sampling port row of each probe is accomplished by a porous filter material which spans the port means of the row. This filter material contains pores which are sized to maintain across the port means a pressure drop which is substantially uniform and relatively large in comparison to any pressure fluctuations along the port means, whereby such fluctuations do not produce any significant fluctuations in the uniform sampling rate along the sampling row. The filter material also blocks entrance into the probe of solids which would soon constrict or block gas flow through the probe passage.

DESCRIPTION OF THE PREFERRED EMBODIMENTS

As noted earlier, present day techniques for sampling gas streams in large ducts, too large for monitoring of the entire flow, tend to fall into two extremes, namely, precise manual sampling surveys at one extreme and flow proportional array sampling at the other extreme. While these sampling techniques are suitable for some sampling applications, they tend to be too complicated, costly, and/or time consuming and laborious for many industrial sampling applications and process control and emissions standards compliance monitoring. The present invention provides a spatial or row average, stationary source sampling technique and apparatus which effectively provides a compromise between the two sampling extremes referred to above and is adapted for such industrial sampling applications.

Figure 1:
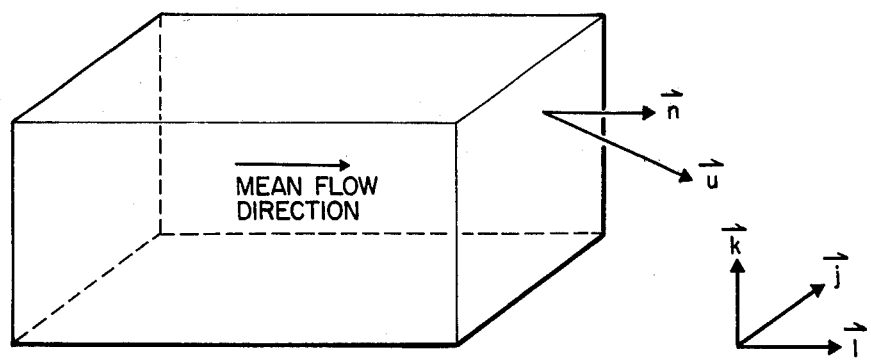
FIGS. 1 and 2 diagrammatically illustrate certain basic stationary source gas flow conditions fundamental to the invention.

A clear and complete understanding of this invention may be best had by considering first the requirements of the current flow proportional sampling technique. To this end, consider the duct shown in FIG. 1, whose four sides and entry and exit planes form a control volume. By definition, the duct sides are solid, so that all fluid must enter through the left plane and leave through the right plane. For simplicity (which does not compromise accuracy), assume that the flow rate into the control volume is always exactly the same as the flow rate out of the control volume. This relation becomes true as the size of the control volume approaches zero. The flow through control volume may then be given as the flow through the exit plane of the control volume:

$$\dot{m} = \int\int_A \rho \vec{u} \cdot \vec{n} \, dA = \overline{\rho u} A \quad (1)$$

where:

$\dot{m}$ = mass flow rate, gm/sec
$\rho$ = local fluid density, gm/cm$^3$ (gas phase only)
$\vec{u}$ = local velocity (vector), m/sec
$\vec{n}$ = unit vector normal to exit plane, dimensionless
$A$ = exit plane area, m$^2$ Flow enters from the left and exits to the right. Velocity at a point in the exit plane is given by $$\vec{u} = u\vec{i} + v\vec{j} + w\vec{k}$$

where:

$\vec{i}, \vec{j}, \vec{k}$ are unit vectors in the directions shown, forming an orthogonal coordinate system and $u, v, w$, are the scalar components of $\vec{u}$ in the $\vec{i}, \vec{j}$, and $\vec{k}$ directions, respectively.

The vector $\vec{n}$ is the unit vector normal to the exit plane, so that $$\vec{n} = \vec{i}$$

and the net flow component out of the duct at the point shown is $u = \vec{u} \cdot \vec{n}$ = scalar velocity component normal to exit plane, m/sec.

This equation represents the total instantaneous gas flow through the control volume. In gas sampling work, it is desirable to know the instantaneous mass flow of a specific constituent $i$, such as $O_2$ or $SO_2$, for control and/or regulatory purposes. For this case, we have $$\dot{m}_i 32 \int\int \rho_i \vec{u} \cdot \vec{n} \, dA \quad (2)$$

where $(\ )_i$ denotes the property relative to species $i$, e.g.,
$\dot{m}_i$ = mass flow of species $i$, gm/sec
$\rho_i$ = mass density of species $i$, gm/cm$^3$ This can be put in terms of normally measured parameters as follows:

$$\rho_i = c_i M_i = c \mu_i M_i \quad (3)$$

where $c$ = global concentration, moles/cm$^3$
$c_i$ = concentration of species $i$, moles of $i$/cm$^3$
$M_i$ = molecular weight of species i, grams of $i$/mole of $i$
$\mu_i$ = mole fraction of species $i$, moles of $i$/mole $$c = RT/p \quad (4)$$

where
R = universal gas constant, gm·m²/mole·sec²·°K
T = absolute temperature, °K
p = absolute pressure, torr Substituting in equation (2) yields:

$$\dot{m}_i = \iint (RT/p)\mu_i M_i \vec{u} \cdot \vec{n} \, dA \quad (5)$$

or $$\dot{m}_i = R M_i A \overline{(T\mu_i u/p)} \quad (6)$$

where the average is defined by correct evaluation of the integral in equation (5). Equation (6) is now in terms of the basic engineering parameters commonly measured in a gas flow. The mole fraction $\mu_i$ is commonly given in units of parts per million for gases such as $SO_x$ and $NO_x$, and in mole percent for $N_2$, $O_2$, $H_2O$, and $CO_2$.

It is common practice to evaluate equation (5) by means of a gas sample traverse. The integration is then approximated by the summation $$\dot{m}_i \doteq RM_i \sum_{n=1}^{N} \frac{T_n}{P_n} (\mu_i)_n u_n \Delta A_n \quad (7)$$

for N area segments. Usually the segments are of equal area, so that $$\dot{m}_i \doteq \frac{A}{N} RM_i \sum_{n=1}^{N} \frac{T_n}{P_n} (\mu_i)_n u_n \quad (8)$$

Figure 2:
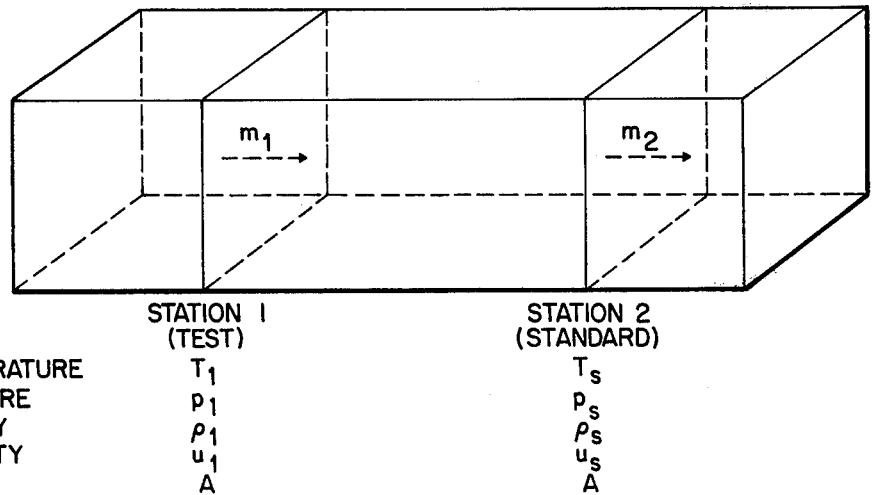

Equation (8) is the practical form of equation (5). It shows that for accurate gas sampling measurements, the local velocity component normal to the sampling plane and the local static pressure and temperature must be masured as well as the local concentration (Note: from this point on, the term $\mu_i$ will be referred to as "concentration" rather than "mole fraction" in accordance with common practice). Temperature and pressure effects are most easily handled through introduction of the concept of "velocity at standard conditions." This is illustrated in FIG. 2. For this control volume, the gas enters at arbitrary pressure and temperature. It then undergoes whatever changes are required in order to emerge uniformly at selected standard conditions, such as at a static temperature of 20° C and at an absolute static pressure of 760 torr. Also by definition, the gas is considered to be chemically fixed and there are no phase changes. This is important from a practical measurement standpoint. It means that the mass flow rate being considered is that of the gaseous components only, since common velocity sensors for operation in a gas stream respond to gas flow. Therefore, defining a gas flow in terms of standard rather than actual conditions implies changes in pressure and temperature only — not composition and phase. Thus, for any one area segment where the velocity and density are considered to be uniform, $$(T/p)u = (T_s/p_s)u_s \quad (9)$$

where
$(\ )_s$ = value at standard atmospheric conditions so that $$\dot{m}_i = \frac{AT_s}{Np_s} RM_i \sum_{n=1}^{N} (\mu_i)_n (u_s)_n \quad (10)$$

or $$\dot{m}_i = \frac{AT_s}{Np_s} RM_i \overline{\mu_i u_s} \quad (11)$$

Thus for the term "proportional sampling" to be truly correct, it should be interpreted as sampling in proportion to the local velocity at standard conditions so that temperature and pressure effects are not ignored.

The proportional gas sampling requirement inherent in equation (11) is the source of significant practical difficulties in the field, since the sampling rate must be changed for each point when standard wet chemistry methods are used. If continuous gas analyzers are used, it is possible to monitor the local value of $\mu_i$ with an analyzer and then multiply by the local velocity to obtain the local mass flow rate. Proportional sampling is represented by the term $\overline{\mu_i u_s}$ in equation (11), which denotes that the true constituent mass flow rate is given by the average of the products of local concentration and local velocity. This is mathematically different from the product of the average concentration and the average velocity:

$$\overline{\mu_i u_s} \neq \overline{\mu_i} \cdot \overline{u_s} \quad (12)$$

Actual equality of equation (12) is guaranteed only if either concentration or velocity is constant in the sampling plane. Actual sampling surveys in rectangular ducts, however, clearly demonstrate that if gas stratification levels are sufficiently low, and there is no direct correlation between regions of high and low concentration and high and low velocity, then the following approximation is valid with a degree of accuracy which is totally satisfactory for many stationary source sampling applications:

$$\overline{\mu_i} \cdot \overline{u_s} \approx \overline{\mu_i u_s} \quad (13)$$

Utilization of the above approximation eliminates the necessity of proportional sampling and permits the use of a relatively simple constant flow rate sampling network, that is a sampling network in which the same sampling rate is maintained at all the gas sampling points of the network. Moreover, gas sampling ($\mu_i$) and volumetric flow ($u_s$) measurement may be performed independently of one another, and in some cases it may be possible to measure volumetric flow in complex ducts with but a single velocity sensor. It is worthwhile to note here that while the validity of the approximation represented by equation (13) has been demonstrated by sampling surveys only in rectangular ducts, these ducts represent the most severe case for the approximation. Accordingly, it is believed that the approximation will hold, with the same degree of accuracy with ducts of most, if not all, other common cross-sections.

Figure 3:
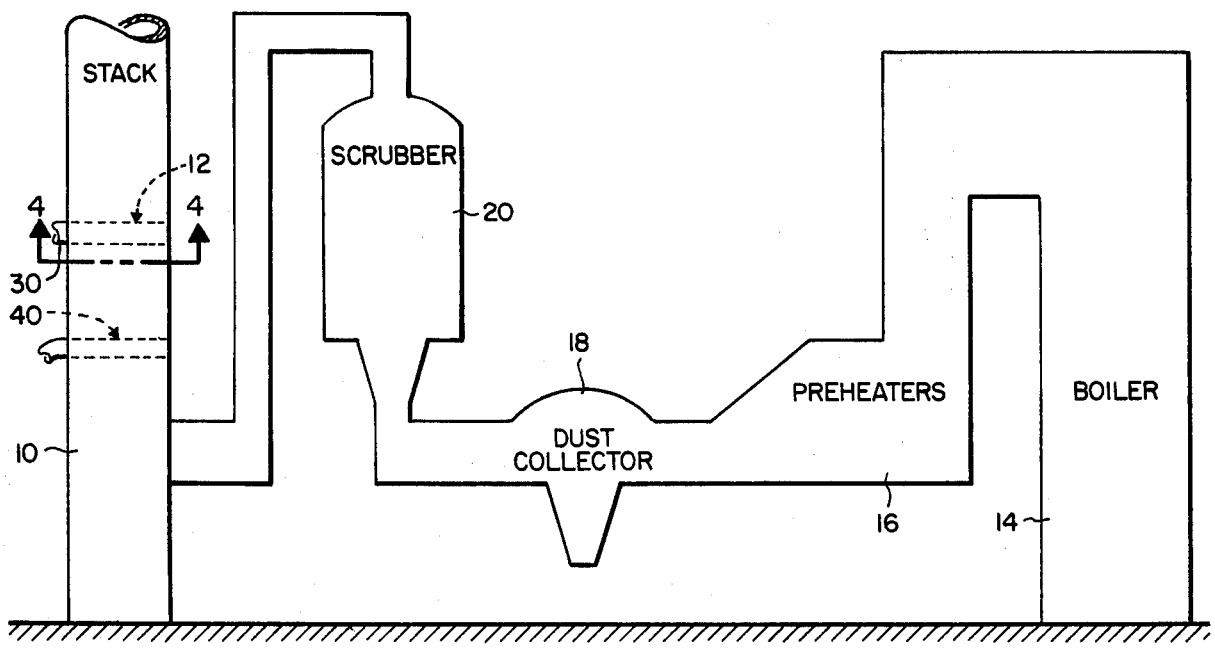
FIG. 3 is a semi-diagrammatic illustration of a gas sampling apparatus according to the invention installed in a stationary source gas flow system.
Figure 4:
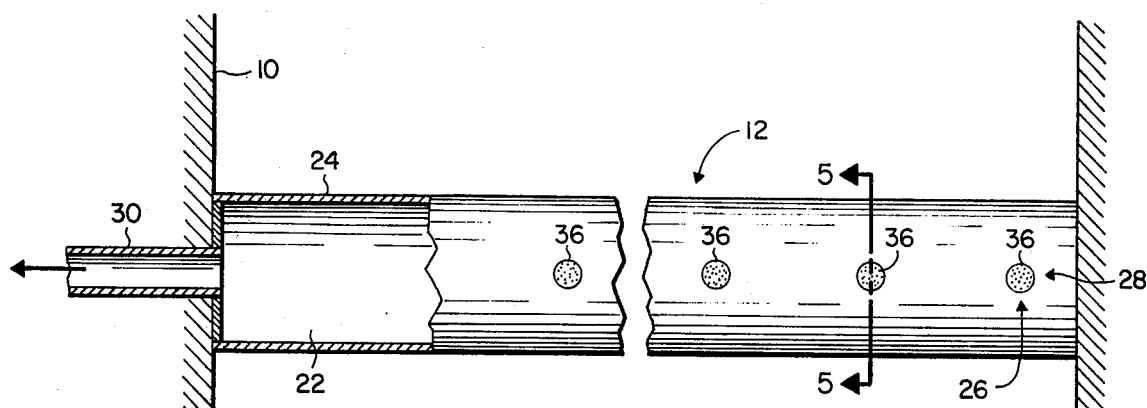
FIG. 4 is an enlarged section taken on line 4—4 in FIG. 3 and illustrating a gas sampling probe in the invention.
Figure 5:
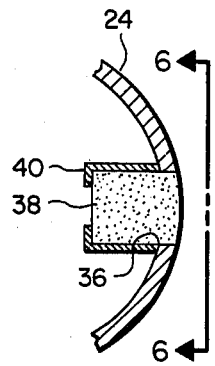
FIG. 5 is a section taken on line 5—5 in FIG. 4.
Figure 6:
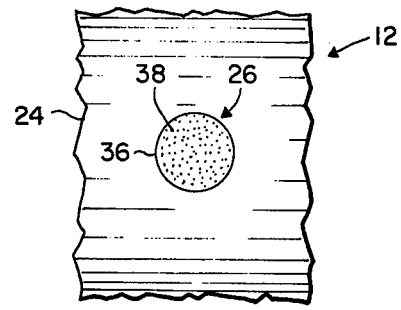
FIG. 6 is a view taken on line 6—6 in FIG. 5.

This invention provides a stationary source gas stream sampling method and apparatus for implementing the sampling approximation represented by equation (13). The sampling technique of the invention is referred to as spatial or row average sampling. According to this spatial or row average sampling technique of the invention, a stationary source gas stream within a flow confining duct 10 (FIG. 3) is sampled with the aid of a tubular sampling probe 12 extending across the stream flow path in a transverse sampling plane of the path. Maximum sampling accuracy is attained by extension of the probe in the direction of maximum stratification in the stream. In the particular sampling application illustrated, the stationary source of the gas is a boiler 14 from which the effluent combustion gas flows through preheaters 16, a dust collector 18, a scrubber 20, and duct 10, which is a stack, to atomsphere.

Figure 9:
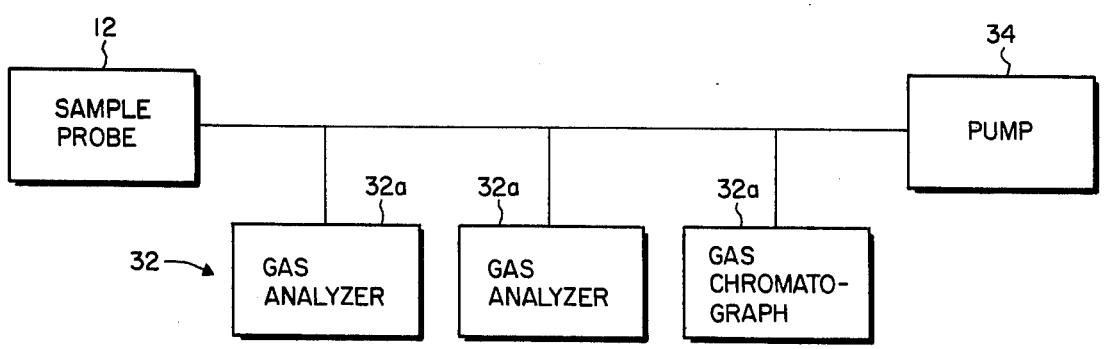
FIG. 9 is a diagram of the gas sampling apparatus.

Sampling probe 10 has a central longitudinal passage 22 bounded circumferentially by a tube wall 24 having sampling port means 26 opening to the probe passage and forming a longitudinal sampling port row 28 in the probe. The probe 12 has an outlet 30 for connection to gas analyzing means 32 (FIG. 9) and to a vacuum source 34 for inducing gas flow into the probe through its port means and flow of the gas from the probe to the analyzing means.

Adaptation of the probe to the approximation sampling concept represented by equation (13) is accomplished by constructing the probe sampling port means 26 in a manner such as to provide a substantially constant sampling rate along the full length of the sampling port row 28. This is accomplished by constructing the port means 26 in a manner such that the pressure drop across the port means is larger by a factor on the order of 10 to 20 than any internal or external pressure fluctuations which occur along the probe during sampling operation and is substantially constant or uniform along the length of the sampling port row.

Figure 7:
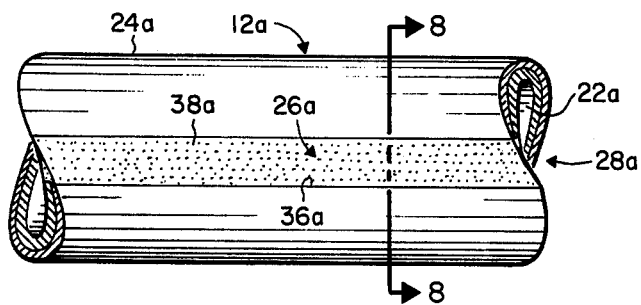
FIG. 7 illustrates a modified sampling probe according to the invention.
Figure 8:
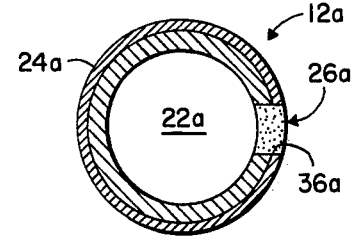
FIG. 8 is a section taken on line 8—8 in FIG. 7.

In the particular inventive embodiments illustrated, the required pressure drop across the sampling port means is produced by a porous filter medium which spans the port means. In the sampling probe 12 of FIGS. 3 through 6, for example, the sampling port means 26 comprises a row of spaced circular ports 36 facing lengthwise of the duct 10. Within each ports 36 is a porous filter insert 38 which seats within a socket 40 joined to the inner side of the probe wall 24 about the port. In the modified sampling probe 12a of FIGS. 7 and 8, the sampling port means 26a, which forms a sampling port row 28a, comprises a single narrow slot-like port 36a extending length-wise of the probe wall 24a and a narrow strip-like porous filter insert 38a within the port 36a.

The porous filter inserts 38, 38a serve a dual purpose. First and foremost, they provide the requisite pressure drop across their sampling ports 36, 36a, that is a pressure drop which is large in comparison to any pressure changes which occur along the probes in operation and is substantially uniform along the sampling port rows 28, 28a. Secondly, the filter inserts block entrance into the probes of any solid particles which would tend to obstruct gas flow through the probes.

It is now evident that the invention provides gas sampling apparatus for a stationary source gas stream including a sampling probe 12, 12a to be installed within a flow duct 10 for the gas. The probe is evacuated by the vacuum source 34 to draw into the probe, through its sampling port means 26, 26a, gas from the stream along the entire length of the sampling port row 28, 28a. The gas entering the probe at the various points along the port row mixes within the probe passage 22, 22a, and the composite sample flows to the gas analyzing means 32. The analyzing means may comprise conventional continuous gas analyzers 32a for measuring selected constituent concentration of the gas stream. the resulting constituent concentration data may then be combined with volumetric flow measurement data obtained by volumetric flow sensing means 40 in the gas stream flow path to obtain the total constituent volumetric data.

Owing to the large magnitude, compared to pressure fluctuations along the probe, and uniformity, along the port rows 28, 28a, of the pressure drop across the sampling port means 26, 26a, sampling of the gas occurs at a substantially constant sampling rate along the full length of the sampling port row, as required for spatial or row average sampling in accordance with the approximation of equation (13). As noted earlier, this row average sampling technique permits independent gas sampling and gas stream volumetric flow measurement whereby the sampling probe 12, 12a and the flow sensor 40 may be independently situated at the best locations for each in the gas flow duct 10. In some instances a single sampling probe and/or flow sensor may suffice for the particular sampling accuracies required. In other cases, a plurality of probes and/or sensors may be necessary. The gas flow line leading from the sampling probe to the gas analyzers may be heat traced, if necessary, to prevent condensation of the sample.

A typical gas sampling probe according to the invention, may have a tubular body on the order of 1-inch in diameter with circular ports 36 (FIGS. 3 through 6) on the order of ½-inch in diameter and containing porous filter inserts 38 constructed of sintered stainless steel. The filter insert 38a of FIGS. 7 and 8 may also be constructed of sintered stainless steel.

I claim:

1. A gas sampling probe for continuous row average sampling of a stationary source gas stream comprising:
    a tubular body to be placed in sampling position in said gas stream;
    said body having a longitudinal passage bounded by a tube wall containing a longitudinal row of sampling ports opening to said passage and an outlet from said passage for connection to gas analyzing means and a vacuum source for evacuating said probe to effect inflow of gas into said probe passage through said ports, mixing of the entering gas within said passage to form composite sample gas, and flow of said composite gas to the gas analyzing means; and
    each port containing a separate porous filter through which gas flow occurs to said probe passage and whose pores are sized to produce a pressure drop across the port which is larger by a factor on the order of 10 to 20 than any pressure changes which occur along said port row and is substantially constant along said port row so as to maintain a substantially uniform sample rate along said port row.

2. A gas sampling probe for continuous row average sampling of a stationary source gas stream comprising:
    a tubular body to be placed in sampling position in said gas stream;
    said body having a longitudinal passage bounded by a tube wall containing sampling port means forming a sampling port row extending lengthwise of said probe and opening to said passage and an outlet from said passage for connection to gas analyzing means and a vacuum source for evacuating said probe to effect inflow of gas into said probe passage through said port means, mixing of the entering gas within said passage to form composite sample gas, and flow of said composite gas to the gas analyzing means; and
    said port means comprising a single long narrow longitudinal slot-like port in said body wall and a porous filter strip in said port through which gas flow occurs to said probe passage, and the pores in said filter strip being sized to provide a pressure drop across the port which is larger by a factor on the order of 10 to 20 than any pressure changes which occur along said port row and is substantially constant along said port row so as to maintain a substantially uniform sample rate along said port row.

3. A continuous row average gas sampling apparatus for a stationary source gas stream comprising:
- a tubular sampling probe to be placed in sampling position in said gas stream and having a longitudinal passage bounded by a tube wall containing a longitudinal row of sampling ports opening to said passage, and an outlet from said passage;
- gas analyzing means connected to said probe outlet;
- vacuum means connected to said probe outlet through said analyzing means for evacuating said probe to effect inflow of gas into said probe passage through said port means, mixing of the entering gas within said passage to form composite sample gas, and flow of said composite sample gas to the gas analyzing means; and
- each port containing a separate porous filter through which gas flow occurs to said probe passage and whose pores are sized to produce a pressure drop across the port which is larger by a factor on the order of 10 to 20 than any pressure changes which occur along said port row and is substantially constant along said port row so as to maintain a substantially uniform sample rate along said port row.

4. A continuous row average gas sampling apparatus for a stationary source gas stream comprising:
- a tubular sampling probe to be placed in sampling position in said gas stream and having a longitudinal passage bounded by a tube wall containing sampling port means opening to said passage and forming a sampling port row extending lengthwise of said probe and opening to said passage, and an outlet from said passage;
- gas analyzing means connected to said probe outlet;
- vacuum means connected to said probe outlet through said analyzing means for evacuating said probe to effect inflow of gas into said probe passage through said port means, mixing of the entering gas within said passage to form composite sample gas, and flow of said composite sample gas to the gas analyzing means; and
- said port means comprising a single long narrow longitudinal slot-like port in said body wall and a porous filter strip in said port through which gas flow occurs to said probe passage, and the pores in said filter strip being sized to provide a pressure drop across the port which is larger by a factor on the order of 10 to 20 than any pressure changes which occur along said port row and is substantially constant along said port row so as to maintain a substantially uniform sample rate along said port row.

* * * * *

UNITED STATES PATENT OFFICE
CERTIFICATE OF CORRECTION

PATENT NO. : 4,047437
DATED : September 13, 1977
INVENTOR(S) : Edward F. Brooks

It is certified that error appears in the above-identified patent and that said Letters Patent are hereby corrected as shown below:

Before BACKGROUND OF THE INVENTION insert --The Government has rights in this invention pursuant to Contract No. 68-02-0636 awarded by the Environmental Protection Agency.--

Column 3, line 45, change "in" to --of--

Column 4, equation (2), change " $\dot{m}_i 32 \iint \rho i \, \vec{u} \cdot \vec{n} \, dA$ "

to -- $\dot{m}_i = \iint \rho i \, \vec{u} \cdot \vec{n} \, dA$ --

Column 7, line 65, change "concentration" to --concentrations--

Column 7, line 65, after the period, change "the" to --The--

UNITED STATES PATENT OFFICE
CERTIFICATE OF CORRECTION

PATENT NO. : 4,047,437
DATED : September 13, 1977
INVENTOR(S) : Edward F. Brooks It is certified that error appears in the above-identified patent and that said Letters Patent are hereby corrected as shown below:

Column 2, line 38, change "preverably" to --preferably--

Column 5, line 40, change "masured" to --measured--

Signed and Sealed this

Twenty-eighth Day of February 1978

[SEAL]

Attest:

RUTH C. MASON
Attesting Officer

LUTRELLE F. PARKER
Acting Commissioner of Patents and Trademarks